United States Patent [19]

Voit

[11] Patent Number: 4,581,204

[45] Date of Patent: Apr. 8, 1986

[54] THIN FILM GAS SENSOR

[75] Inventor: Helmut Voit, Munich, Fed. Rep. of Germany

[73] Assignee: Siemens Aktiengesellschaft, Berlin and Munich, Fed. Rep. of Germany

[21] Appl. No.: 593,875

[22] Filed: Mar. 27, 1984

[30] Foreign Application Priority Data

Jun. 2, 1983 [DE] Fed. Rep. of Germany ....... 3322481

[51] Int. Cl.$^4$ ............................................. G01N 27/12
[52] U.S. Cl. ......................................... 422/90; 73/23; 204/192 S; 338/34; 422/98
[58] Field of Search ...................... 422/88, 90, 94–98; 73/23; 338/34; 204/421, 424

[56] References Cited

U.S. PATENT DOCUMENTS 4,197,089 4/1980 Willis et al. ........................ 422/98 X
4,314,996 2/1982 Sekido et al. ......................... 422/98

FOREIGN PATENT DOCUMENTS 0024679 3/1981 European Pat. Off. .............. 422/98
0046989 3/1982 European Pat. Off. .
49-103699 1/1974 Japan ..................................... 422/98
0020577 4/1982 Japan ................................ 422/98 M

OTHER PUBLICATIONS

"Current Topics in Materials Science", vol. 1, (1978), pp. 496–508.

Primary Examiner—Arnold Turk
Attorney, Agent, or Firm—Hill, Van Santen, Steadman & Simpson

[57] ABSTRACT

A thin film gas sensor for the detection and measurement of gaseous hydrocarbon contaminants having double and triple bonds in air by means of semiconductive tungsten oxide. The invention also relates to a method for manufacturing such a thin film gas sensor. The substrate for the tungsten oxide thin film consists of a lithium niobate monocrystal preferably oriented in the (001) direction. The gas sensor responds very sensitively to acetylene, responds less sensitively to hydrocarbons having double bonds, and exhibits practically no response to saturated hydrocarbons.

6 Claims, 2 Drawing Figures

THIN FILM GAS SENSOR

BACKGROUND OF THE INVENTION

1. Field of the Invention

The present invention relates to the manufacture of high sensitivity, high stability thin film gas sensors for the detection and measurement of gaseous hydrocarbon contaminants having double and triple bonds in air. The sensor employs semiconductive tungsten oxide on a substrate of a lithium niobate monocrystal. The electrical resistance of the tungsten oxide layer is measured as a function of the type and concentration of the gas to be detected.

2. Description of the Prior Art

A true selectivity for a specific gas is difficult to achieve due to the functional principle of gas sensors utilizing semiconductor metal oxides. Accordingly, some other measuring methods must be used, for example, gas chromatography or infrared absorption. In each instance, these measuring methods require a far higher expenditure of money and time. When, however, a gas sensor is to be employed only in alarm and measuring devices having lower precision for monitoring the occurrence of undesirable or dangerous gases, then the metal oxide gas sensors have distinct advantages because they can be applied to many measuring locations without great expense and can be simultaneously monitored.

Depending on the preparation, material selection, and the various additives present as well as on operating parameters, various sensitivities are obtained using metal oxide gas sensors for various gases.

A gas sensor of the type described is illustrated, for example, in European Patent Application No. 0 046 989 and can be employed for the detection and measurement of gaseous hydrocarbon contaminants in the air. Hydrocarbon gases such as methane, propane, butane, ethylene, acetylene and even hydrogen are generally detected with this gas sensor on the basis of the semiconductive tungsten oxide film on substrates of silica glass, oxidized silicon, or a ceramic. The particular sensitivity for specific hydrocarbon compounds has not been identified.

The European Patent Application No.0 046 989, the disclosure of which is hereby incorporated by reference, illustrates a structure which is applicable for the present invention. It consists of a substrate of silica glass, oxidized silicon or a ceramic. On the opposite side of the substrate, i.e., immediately below the substrate is a surface that is highly conducting and is provided with spaced metal contacts for direct heating.

The thin film of sputtered tungsten oxide appears immediately above the silicon dioxide layer. A layer of precious metal such as platinum appears over the tungsten oxide film as an activator. Electrodes are bonded to the thin film of tungsten oxide, spaced by the layer of precious metal.

SUMMARY OF THE INVENTION

The present invention seeks to provide a thin film gas sensor of the type described which is specifically employable for contaminants in air consisting of gaseous hydrocarbon compounds having double and triple bonds and, in particular, for the detection of acetylene.

The invention is also concerned with providing a method for the manufacture of the thin film sensor.

In accordance with the present invention, there is provided a substrate consisting of a lithium niobate monocrystal ($LiNbO_3$) and a thin film of tungsten oxide is generated on this substrate by means of reactive high frequency (HF) sputtering.

Particularly good results are obtained when the substrate consists of a lithium niobate monocrystal oriented in the (001) direction.

The tungsten oxide thin film whose thickness lies in the range from 100 to 1000 nm is produced on the monocrystalline lithium niobate substrate by means of reactive HF sputtering using a metallic tungsten target in an inert gas atmosphere having an oxygen concentration of 1 to 10% at a substrate temperature of 400° C. with a sputtering rate of about 10 nm/min. A good crystallinity and adhesiveness of the layer is achieved by means of a thermal aftertreatment with oxygen at about 600° C. for a time duration of about 100 hours. The tungsten oxide thin film can be activated by means of a precious metal such as platinum or metal oxide, whereby the activator layer does not cover any larger contiguous regions of the surface, does not influence the overall conductivity, and has no direct connection to the measuring contacts.

The present invention provides a gas sensor which responds very sensitively and quickly to acetylene with its triple bonds, responds less sensitively to hydrocarbons having double bonds and responds very little to methane or its homologues.

Adsorption and catalysis processes are both involved in the indication process. It is known that these surface processes are highly dependent on the structure and orientation of the adsorber. The structure of tungsten oxide ($WO_3$) can be derived from the perovskite structure $ABO_3$, wherein the A-locations remain unoccupied. The B-cations, tungsten in this case, are octahedrally surrounded by oxygen ions; the $WO_6$ octahedrons are linked via corners. Due to distortions and mutual tilts of these octahedrons, the real structure of $WO_3$ no longer has cubic symmetry but the deviations of the angles and lengths from the ideal cubic values are only slight. An averaged "cubic" lattice constant of the triclinic or, respectively, monoclinic $WO_3$ modification amounts to about 3.7 A° through 3.8 A°.

The lithium niobate structure can also be analogized to corner-linked octahedrons, $NbO_6$ octahedrons in this case. With eight formula units per elementary cell, the pseudo-cubic, rhombohedric elementary cell thereby occurring has a lattice constant of 7.532 A° (see A. Räuber, Chemistry and Physics of Lithium Niobate, in E. Kaldis (Ed.), Current Topics in Materials Science, Vol. 1, North Holland Publishing Company, 1978). In the idealized, cubic description having one formula unit per elementary cell also employed in the case of $WO_3$, this corresponds to a lattice constant of 3.766 A° . An ordered growth of $WO_3$ layers on $LiNbO_3$ substrates is thus to be expected under suitable manufacturing conditions.

The manufacture of the $WO_3$ layers and of the gas sensor arrangement is described in detail in the initially cited European patent application No. 0 046 989. A thin film specifically responding to acetylene is obtained when the substrate temperature is maintained at about 400° C. and the thickness of the layer deposited is about 200 nm, as set forth in the preferred embodiment described subsequently.

X-ray diffraction investigations confirm that the layers grow highly ordered on the $LiNbO_3$. Only the (001)

reflex of $WO_3$ is measurable; the (001) of $LiNbO_3$ is not present due to the cancellation law, but the first monocrystalline reflex from the substrate is (002).

The layers have very high resistance properties. At temperatures up to 400° C., currents of only less than 10 nA in air could be measured with an applied voltage of 1 Volt at a frequency of 35 Hz. The conductivity increases noticeably only at higher temperatures.

BRIEF DESCRIPTION OF THE DRAWINGS

A further description of the present invention will be made in conjunction with the attached sheets of drawings in which.

DESCRIPTION OF THE PREFERRED EMBODIMENTS

Figure 1:
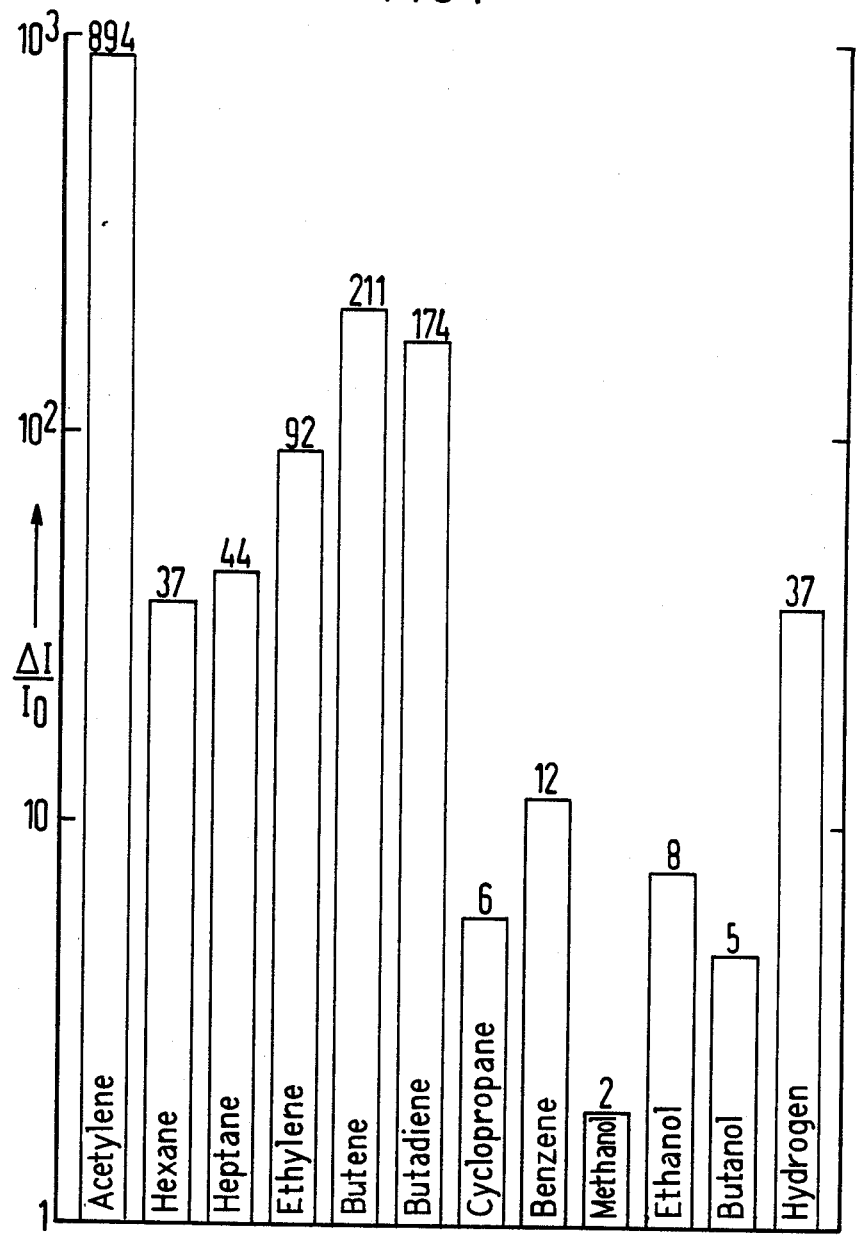
FIG. 1 is a graph illustrating the sensitivity to different gases at a measuring temperature of 300° C.
Figure 2:
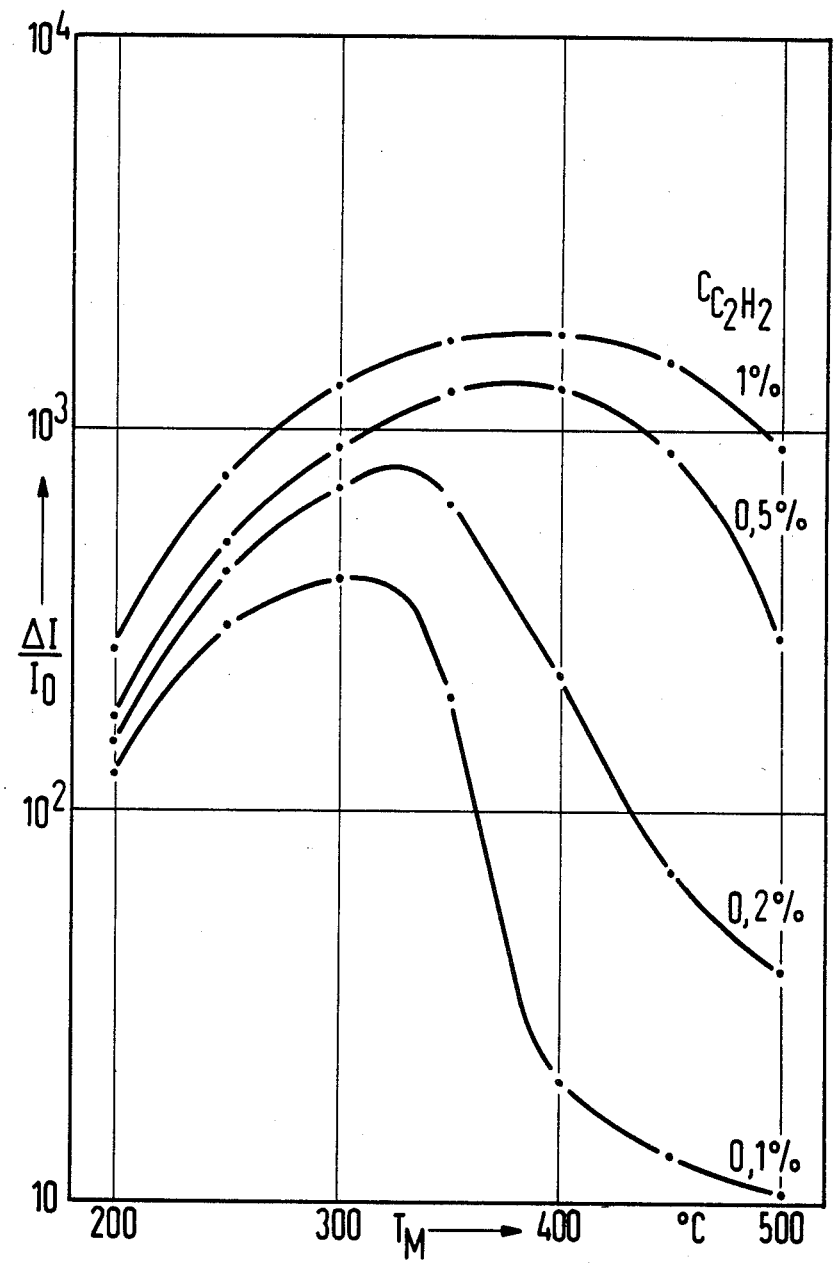
FIG. 2 illustrates the sensitivity to acetylene as a function of the measuring temperature $T_M$. The applied voltage was 1 Volt, at a frequency of 35 Hz.

The sensitivity plotted in FIGS. 1 and 2 is defined as the relative current change $\Delta I/I_0$. In FIG. 1, the measured gas concentration amounted to 0.2%. When various gaseous hydrocarbons were placed in proximity to the sensor, there were noticeable differences over specimens that were made with amorphous substrate material. Saturated hydrocarbons were either not indicated or only weakly indicated at temperatures of 300° to 400° C. This is in contrast to the known $WO_3$ thin film sensors which, for example, show very high sensitivity toward butane. Hydrocarbons having double or triple bonds, by contrast, were readily and quickly indicated. The sensors of the present invention also have low sensitivity toward alcohols and organic solvents. As may be seen from FIG. 1, hydrogen responds only weakly whereas hydrogen is detected with extreme sensitivity by all hitherto investigated sensors. As an example, sensitivities usually exceeding 10,000 are common for a hydrogen concentration of 0.2%.

Acetylene was investigated more thoroughly in terms of its influence on the $WO_3$ layers. FIG. 2 shows the temperature curve of the sensitivity for different measured gas concentrations. The "true" sensitivities are even higher since, with an extremely low base current $I_0$, its measurement is influenced by various parasitic effects. At 300° C., the response and decay times lie in the second range. In contrast to sensors using amorphous substrates, no poisoning due to sulfur compounds such as tetrahydrothiophene could be observed with the sensors of the present invention.

It will be understood that various modifications can be made to the described embodiments without departing from the scope of the present invention.

I claim as my invention:

1. A thin film gas sensor having high sensitivity and high stability for measuring contaminants of double bonded and triple bonded hydrocarbons in air comprising:
   a substrate comprising a lithium niobate monocrystal and
   a thin film of semiconductive tungsten oxide over said substrate, said thin film being generated on the substrate by means of reactive high frequency sputtering, and being no more than 1000 nm in thickness.

2. A gas sensor according to claim 1 in which:
   said substrate consists of a lithium niobate crystal oriented in the (001) direction.

3. A gas sensor according to claim 1 wherein the thickness of the sputtered tungsten oxide film is in the range from 100 nm to 1000 nm.

4. A gas sensor according to claim 1 wherein said tungsten oxide layer is activated by the presence of a precious metal.

5. A gas sensor according to claim 1 wherein said tungsten oxide layer is activated by the presence of a metal oxide.

6. A gas sensor according to claim 4 wherein said precious metal is platinum.

* * * * *